United States Patent [19]
Alvarez

[11] Patent Number: 5,154,184
[45] Date of Patent: Oct. 13, 1992

[54] ADJUSTABLE ANTI-SNORING APPARATUS

[76] Inventor: Ramiro M. Alvarez, 2836 Parkside Dr., Fremont, Calif. 94536

[21] Appl. No.: 760,388

[22] Filed: Sep. 16, 1991

[51] Int. Cl.⁵ .............................................. A61F 5/56
[52] U.S. Cl. ................................................... 128/848
[58] Field of Search ............................ 128/857–863, 128/848

[56] References Cited

U.S. PATENT DOCUMENTS

| | | | |
|---|---|---|---|
| 2,589,504 | 3/1952 | Miller | 128/857 |
| 2,867,212 | 1/1959 | Nunn, Jr. | 128/848 |
| 3,132,647 | 5/1964 | Corniello | 128/848 |
| 3,211,143 | 10/1965 | Grossberg | 128/862 |
| 3,434,470 | 3/1969 | Strickland | 128/848 |
| 3,448,738 | 6/1969 | Berghash | 128/861 |
| 3,692,025 | 9/1972 | Greenberg | 128/857 |
| 3,864,832 | 2/1975 | Carlson | 128/862 |
| 4,169,473 | 10/1979 | Samelson | 128/848 |
| 4,170,230 | 10/1979 | Nelson | 128/859 |
| 4,196,724 | 4/1980 | Wirt et al. | 128/860 |
| 4,262,666 | 4/1981 | Nelson | 128/203.23 |
| 4,304,227 | 12/1981 | Samelson | 128/848 |
| 4,593,686 | 6/1986 | Lloyd et al. | 128/848 |
| 4,676,240 | 6/1987 | Gardy | 128/848 |
| 5,046,512 | 9/1991 | Murchie | 128/848 |

FOREIGN PATENT DOCUMENTS

| | | |
|---|---|---|
| 65194 | 2/1892 | Fed. Rep. of Germany . |
| 2704709 | 11/1977 | Fed. Rep. of Germany . |
| 751281 | 6/1956 | United Kingdom ............... 128/848 |
| 1248474 | 10/1971 | United Kingdom . |

Primary Examiner—Robert A. Hafer
Assistant Examiner—Kevin G. Rooney
Attorney, Agent, or Firm—William W. Haefliger

[57] ABSTRACT

An anti-snoring apparatus comprising receptacle structure configured for reception and retention of outer extent of the user's tongue; shield structure shaped to be received and retained on the tongue receptacle structure and positioned just forward of the user's lip or lips, and attachment structure for adjustably attaching the shield structure to the receptacle structure to permit selective adjustment of the position of the receptacle structure relative to the tongue forward extent whereby the tongue may be comfortably positioned and retained in the receptacle structure; whereby snoring is reduced as the tongue is brought forward, out of the mouth, and incremental forward movement of the shield will move the tongue further forward, with lessened airway obstruction.

12 Claims, 2 Drawing Sheets

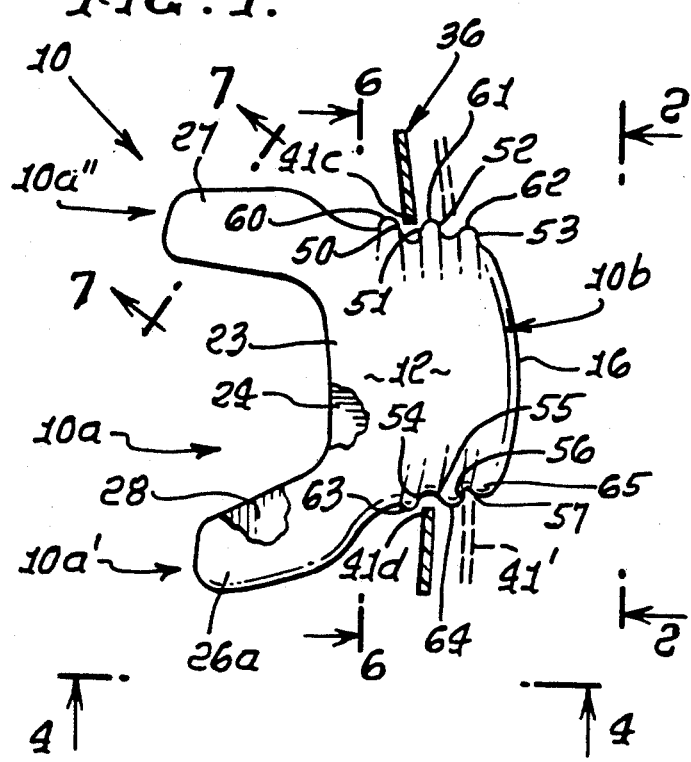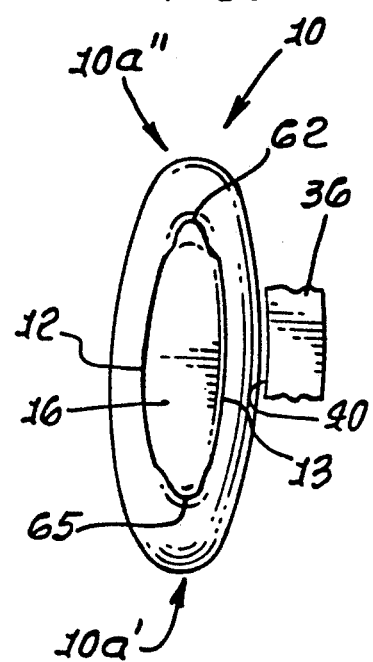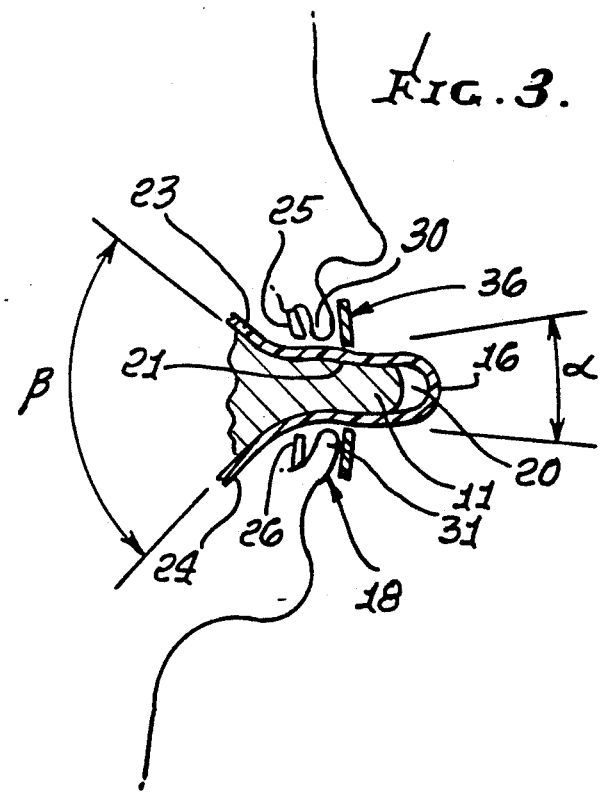

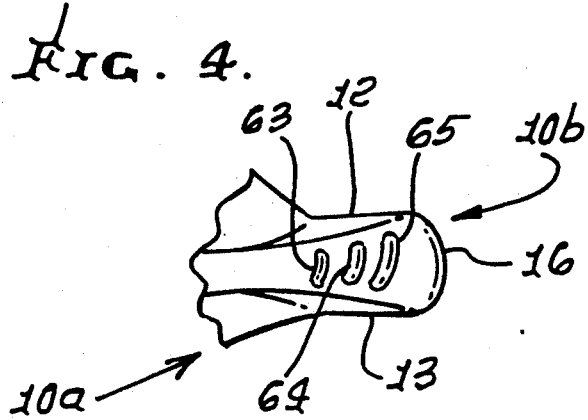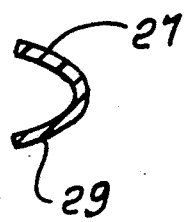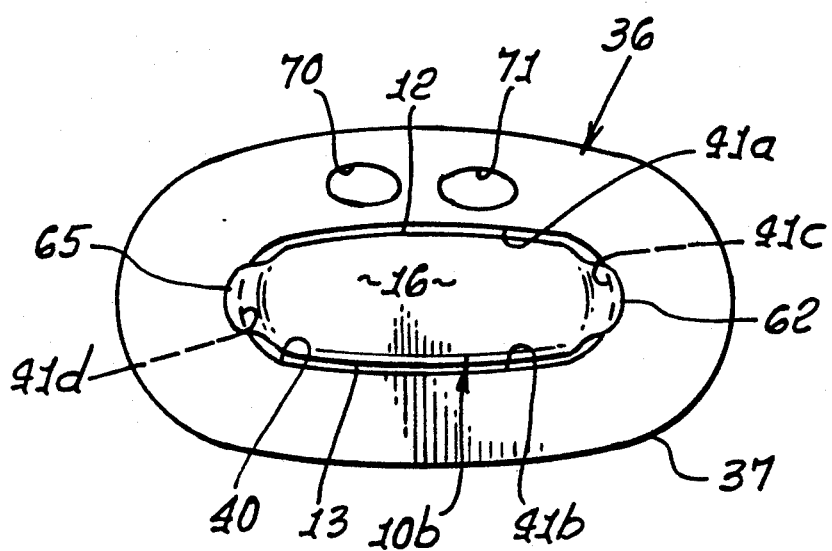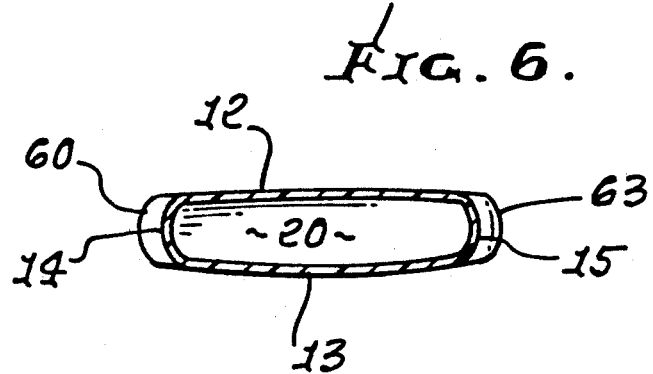

ADJUSTABLE ANTI-SNORING APPARATUS

BACKGROUND OF THE INVENTION

This invention relates generally to apparatus for treating snoring to minimize same. More particularly, it concerns improvements in tongue position control in such apparatus.

Prior devices for controlling snoring include those disclosed in U.S. Pat. Nos. 4,169,473; 4,593,686 and 4,304,227. Certain of such devices provide for reception of the tongue in a hollow formed by a mouth-retained holder. One problem presented by such devices lies in the lack of fit of the device to the user's tongue; for example, mouth retention of the hollow device dictates the position of the tongue socket, whereby a longer tongue is not properly or comfortably accommodated. Such prior devices also are characterized by other problems and difficulties.

SUMMARY OF THE INVENTION

It is a major object of the present invention to provide an improved anti-snoring device free from the problems and difficulties associated with prior devices. Basically, and as will appear, the improved apparatus includes a) receptacle means configured for reception and retention of outer extent of the user's tongue, and to be retained by the user's mouth, b) shield means shaped to be received and retained outwardly of the user's lip, c) and attachment means for adjustably attaching the shield means to the receptacle means to permit selective adjustment of the position of the shield means relative to the tongue forward extent whereby the tongue may be comfortably positioned and retained in the receptacle means, d) whereby snoring is reduced as the tongue is brought forward, out of the mouth, and incremental forward movement of the shield will move the tongue further forward, with lessened airway obstruction.

Typically, the receptacle means has a forward portion, and the retention means projects outwardly of and about the forward portion, sidewardly of the receptacle means.

A further object includes the provision of a shield means extending at least part way about the receptacle means, and to have selective attachment to the latter. The shield may include upper and lower portions to fit outwardly of the user's upper and lower lips. The shield may be loosely carried by the receptacle means to provide breathing passages therebetween, and to allow limited tongue positioning of the receptacle means relative to the shield.

Yet another object of the invention is to provide notches on the retention means to be presented sidewardly for selected engagement with the shield structure. In this regard, the notches may be carried by a forward portion of the receptacle structure, and are spaced to align the receptacle relative to the shield. Also, the user begins by positioning the shield at first notches nearest the face; and the shield can be progressively advanced forwardly, away from the lips, until snoring reduction and tongue comfort are achieved.

These and other objects and advantages of the invention, as well as the details of an illustrative embodiment, will be more fully understood from the following specification and drawings, in which:

DRAWING DESCRIPTION

FIG. 1 is a top plan view of the apparatus incorporating the invention;

FIG. 2 is a right side view taken on lines 2—2 of FIG. 1;

FIG. 3 is a vertical section taken through the device when in use;

FIG. 4 is a side view taken on lines 4—4 of FIG. 1;

FIG. 5 is an enlarged end view showing loose interfit between a shield and tongue receptacle means;

FIG. 6 is a section taken on lines 6—6 of FIG. 1; and

FIG. 7 is a section taken on lines 7—7 of FIG. 1.

DETAILED DESCRIPTION

In the drawings, a one-piece receptacle means is shaped for reception and retention of the forward extent 11 of the user's tongue. Such receptacle means 10 has a "C" or crescent-shaped rearward section 10a, and a pocket-shaped forward section 10b integral with 10a. The forward section has upper and lower generally parallel walls 12 and 13, opposite side walls 14 and 15, which are outwardly convex, and a front wall 16, which is forwardly convex and merging with 12 and 13, and with 14 and 15. Forward section 10b is sized to project forwardly of the user's lips 18, seen in FIG. 3, with the tongue 11 resting comfortably in the cavity or compartment 20 defined by walls 12–16. Walls 12 and 13 flare forwardly at a small angle $\alpha$ (see FIG. 3) from a narrowed region 21, proximate joinder of sections 10a and 10b. Region 21 lightly retains the user's tongue in position, and allows tongue expansion forward of that region. Angle $\alpha$ is between about 2° and 10°.

The rearward crescent section 10a has upper and lower walls 23 and 24 that flare apart, rearwardly, at an enable $\beta$, to fit the user's mouth, inwardly of upper and lower front teeth 25 and 26, where $\beta > \alpha$. $\beta$ is typically between about 15° and 35°. Also, rearward section 10a has laterally extending and rearwardly diverging subsections or lobes 10a' and 10a'' which fit the rearward curvature of the user's left and right, and upper and lower teeth regions. Thus, upper walls 26a and 27 of sub-sections 10a' and 10a'' fit inwardly of the user's upper teeth at right and left sides of the mouth; and lower walls 28 and 29 of sub-sections 10a' and 10a'' fit inwardly of the user's lower teeth at right and left sides of the mouth. The upper and lower front lips appear at 30 and 31 in FIG. 3, and upper and lower front teeth at 25 and 26.

In accordance with a further aspect of the invention, a shield or retention means is provided, and shaped, to be retained outwardly of the user's upper lip, and also outwardly of user's lower lip. As illustrated, the shield means preferably has the form of a shield 36 of wall edge outline 37 and having a wall thickness about the same as the wall thickness of receptacle means 10, i.e., about ⅛ inch. The receptacle means and shield are separate parts to be relatively adjustable for mouth and tongue comfort, and may consist of molded plastic material.

The shield defines an oval shaped opening 40 to receive and fit over the forward section 10b of the receptacle means, in an adjustable manner, and may engage the user's upper and lower lips. Note inner edge 41 of that opening, having elongated upper and lower stretches 41a and 41b concave toward 12 and 13 respectively (see FIG. 5). Air passages 70 and 71 allow breathing of air through those passages while the apparatus is being worn, one or both of those passages allow air to pass in different adjusted positions of the shield on the tongue receptacle.

Attachment means is provided for adjustably attaching the shield means to the receptacle means to permit selective adjustment of the position of the receptacle means relative to the tongue forward extent whereby the tongue may be comfortably positioned and retained in the receptacle means. Such attachment means may advantageously take the form of notches presented sidewardly of the receptacle means. See in FIG. 1, for example, forwardly and rearwardly spaced notch-defining shoulders 50 and 51, and 52 and 53 at side 14 of 10b, and forwardly and rearwardly spaced notch-defining shoulders 54 and 55, and 56 and 57 at side 15 of 10b.

The shield edge 41c is seen adjusted rearwardly to fit the notches between 50 and 51 in FIG. 1, and edge 41d fitting the notch between 54 and 55. If desired, the flexible shield can be adjusted forwardly (see broken lines 41') so that its edge 41c fits the notch between 52 and 53, and edge 41d between 56 and 57. Thus, comfort of the wearer's tongue retention, as during sleep, is facilitated while breathing through one or both passages 70 and 71 referred to below remains possible. In this regard, the shield is retained in position on the receptacle which is retained in position by the mouth, and the tongue is positioned comfortably in and by the receptacle, which may be adjusted relative to the shield, as desired.

The notches and shoulders may be formed by edge flanges, as shown, and indicated at 60–65. Note also shield through openings 70 and 71 for air passage past the upper lip. Note that the user's lips are free to flex and are not outwardly constrained or overlain by the apparatus.

See also the following advantages:

1. The generic design of appliance reduces cost to the patient.
2. The tongue compartment may be made in three sizes, regular, large, and extra large to better accommodate a variety of tongue sizes.
3. The method of extending the tongue is controlled by stops in each side of the tongue compartment.
4. The overall size of the appliance is relatively small, thus more comfortable. It relieves psychological stress, allowing muscles to relax and enable better treatment of snoring.
5. The design of the tongue retention shield allows those who are mouth breathers to breath normally, without need for bulky airways. It is also easy to breathe around the device.
6. The appliance is designed in the posterior area to allow minimal vertical opening, which will avoid TMJ problems.
7. The thickness, in the posterior region, of the vinyl (plastic) material is such that it will prevent damage caused by bruxism.
8. The tongue pouch is so designed as to allow better tongue control, by grasping and keeping it in a protrusive position determined by the labial shield.
9. The device is so designed that it does not need the services of a professional for adaptation. It can be fitted by the patient for maximum benefit.
10. The appliance may be made in colors so that it may be identified easily. Its opaqueness makes it more attractive to wear.
11. The appliance is marked so that it cannot be inserted in the wrong manner, and with holes for breathing and reinforcement flanges to determine the correct position. Note breathing holes 70 and 71.

I claim:

1. In anti-snoring apparatus, the combination comprising
   a) receptacle means configured for reception and retention of forward extent of the user's tongue, and to be retained by the user's mouth,
   b) shield means shaped to be received and retained outwardly of the user' lip,
   c) and attachment means for adjustably attaching the shield means to said receptacle means to permit selective adjustment of the position of the shield means relative to the tongue forward extent whereby the tongue may be comfortably positioned and retained in said receptacle means,
   d) whereby snoring is reduced as the tongue is brought forward, out of the mouth, and incremental forward movement of the shield will move the tongue so as to provide lessened airway obstruction.

2. The combination of claim 1 wherein said receptacle means has a forward portion, and said shield means projects outwardly of and about said forward portion, sidewardly of said receptacle means.

3. The combination of claim 2 wherein said shield means extends about the receptacle means.

4. The combination of claim 1 wherein said attachment means comprises notches which are presented sidewardly of said receptacle means.

5. The combination of claim 4 wherein said receptacle means has a forward portion and said notches are on said forward portion.

6. The combination of claim 5 wherein said shield means has an inner edge portion adjustably receivable in said notches.

7. The combination of claim 6 wherein said shield means has at least one through opening to provide breathing passage means therebetween.

8. The combination of claim 6 wherein the shield means comprises a flexible plastic sheet.

9. The combination of claim 8 wherein the receptacle means has flexible plastic walls, and is oval shaped in cross section laterally between said notches.

10. The combination of claim 6 wherein said shield means defines air passing openings.

11. The combination of claim 9 wherein said walls flare rearwardly of said notches.

12. The combination of claim 1 wherein said receptacle means has rearwardly flaring lobes, and is rearwardly crescent-shaped.

* * * * *